United States Patent [19]

Nguyen

[11] Patent Number: 5,612,321
[45] Date of Patent: Mar. 18, 1997

[54] ANTIOXIDANT GRAFTED POLYSACCHARIDES

[75] Inventor: Tuyen T. Nguyen, New Castle, Del.

[73] Assignee: Hercules Incorporated, Wilmington, Del.

[21] Appl. No.: 493,854

[22] Filed: Jun. 22, 1995

[51] Int. Cl.$^6$ .......................... A61K 31/715; A61K 6/00; C08B 37/00; C08B 16/00
[52] U.S. Cl. .................. 514/54; 514/56; 514/57; 514/58; 514/59; 514/60; 424/401; 602/49; 536/21; 536/30; 536/43; 536/44; 536/56; 536/63; 536/66; 536/84; 536/88; 536/90; 536/93; 536/94; 536/103; 536/106; 536/110; 536/111; 536/112; 536/119; 536/120; 536/124
[58] Field of Search .................. 536/21, 43, 44, 536/30, 56, 63, 66, 84, 88, 90, 93, 94, 103, 106, 110, 111, 112, 119, 120, 124; 424/401; 602/49; 514/54, 56, 57, 58, 59, 60

[56] References Cited

U.S. PATENT DOCUMENTS

| | | | |
|---|---|---|---|
| 4,582,865 | 4/1986 | Balazs et al. | 524/29 |
| 4,605,691 | 8/1986 | Balazs et al. | 524/27 |
| 4,636,524 | 1/1987 | Balazs et al. | 514/781 |
| 4,713,448 | 12/1987 | Balazs et al. | 536/55.1 |
| 4,716,154 | 12/1987 | Mälson et al. | 514/54 |
| 4,716,224 | 12/1987 | Sakurai et al. | 536/55.1 |
| 4,772,419 | 9/1988 | Mälson et al. | 252/315.1 |
| 4,795,741 | 1/1989 | Leschiner et al. | 514/21 |
| 4,863,907 | 9/1989 | Sakurai et al. | 514/56 |
| 4,886,787 | 12/1989 | deBelder et al. | 514/57 |
| 4,957,744 | 9/1990 | della Valle et al. | 424/401 |
| 5,128,326 | 7/1992 | Balazs et al. | 514/54 |
| 5,166,331 | 11/1992 | della Valle et al. | 536/55.1 |
| 5,356,883 | 10/1994 | Kuo et al. | 514/54 |
| 5,358,973 | 10/1994 | Lindblad et al. | 514/777 |
| 5,384,187 | 1/1995 | Uemura et al. | 428/262 |
| 5,429,856 | 4/1995 | Krueger et al. | 604/370 |
| 5,492,943 | 2/1996 | Stempel | 523/111 |

FOREIGN PATENT DOCUMENTS

| | | |
|---|---|---|
| 0341745 | 11/1989 | European Pat. Off. . |
| 0507604 | 10/1992 | European Pat. Off. . |

OTHER PUBLICATIONS

Merck Manual of Diagnosis and Therapy—10th Ed., 1992, pp. 1338–1342.
Balazs et al., J.Equine Vet. Sci., 5, pp. 217–228 (1985).
Weiss et al., Semin. Arthritis Rheum., 11, p. 143 (1981).
Namiki et al., Int. J. Clin. Pharmacol., Therapy Toxicology, 20, p. 501 (1982).
Grecomoro et al., Pharmatherapeutica, 5, p. 137 (1987).
Bragantini et al. Clinical Trials J., 24, p. 333 (1987).
Dahlberg et al., Arthritis & Rheumatism, 37, p. 521 (1994).
Brown et al., Exp. Physiol., 76, p. 1251 (1991).
McCord, Sciencee, 185, p. 529 (1974).
Wong et al., Inorganic Biochemistry, 14, p. 127 (1981).
Miller et al., J. Bone & Joint Surgery, 40, p. 636 (1958).
Chemical Abstracts, vol. 119, No. 9, Aug. 30, 1993 Abstract No. 85647.

*Primary Examiner*—John Kight
*Assistant Examiner*—Kathleen Kahler Fonda
*Attorney, Agent, or Firm*—Martin F. Sloan

[57] ABSTRACT

Grafted polysaccharide compositions comprising polysaccharides grafted with antioxidants on at least one hydroxyl group of the polysaccharide. The use of antioxidant grafted polysaccharides or antioxidant grafted crosslinked polysaccharides as a treatment for arthritis, as a drug delivery vehicle, to reduce the incidence of post-operative adhesion formation, to promote the healing of chronic wounds and ulcers, and as a component of cosmetic formulations.

84 Claims, No Drawings

ANTIOXIDANT GRAFTED POLYSACCHARIDES

FIELD OF THE INVENTION

This invention relates to polysaccharides grafted with antioxidants, and preferably hyaluronic acid or crosslinked hyaluronic acid grafted with hindered phenols.

BACKGROUND OF THE INVENTION

The synovial fluid found in mammalian joints functions as a lubricant and shock absorber. The most important component of the synovial fluid is sodium hyaluronate, which makes the greatest contribution to the mechanical properties of the fluid. Hyaluronic acid is a naturally occurring high molecular weight glycosaminoglycan having a repeating disaccharide unit of 2-amino-2-deoxy-3-o-($\beta$-D-glucopyranosyluronic acid)-D-glucose. The disaccharides are joined to form an unbranched, uncrosslinked polysaccharide chain by $\beta1 \rightarrow 4$ glucosidic bonds. In addition to its presence in synovial fluids, hyaluronic acid occurs in cell coats, pericellular gels, the extracellular matrix substance of connective tissues of vertebrates, the vitreous humor of the eye, human umbilical cord tissue, rooster combs and in some bacteria.

During inflammation of a joint caused, for example, by osteo- or rheumatoid arthritis both the molecular weight of hyaluronic acid and its concentration are reduced. This lowering of molecular weight decreases the ability of synovial fluid to act as a shock absorber, and thus the fluid does not provide adequate protection for the cartilage of the joint. Moreover, the lowering of molecular weight also reduces viscosity and thus promotes leakage from the joint. In the case of advanced arthritis the cartilage is eroded away, leading to pain when the joint is in motion (see for example, "The Merck Manual of Diagnosis and Therapy-16th Edition", p 1338–42).

One of the causes for the lowering of molecular weight and for the high rate of loss of sodium hyaluronate from the synovial cavity, is the degradation of the molecule by hydroxyl radicals. Hydroxyl radicals come from two sources. The primary source is white blood cells which enter the joints when they are inflamed, and release xanthine peroxidase and other enzymes to form superoxide anion, hydrogen peroxide and hypochlorite, which upon breakdown form hydroxyl radical. Another source for hydroxyl radical is the reduction of oxygen by reducing agents in the presence of iron. A common reducing agent in the body is ascorbic acid. Oxygen is reduced by iron(II) to form superoxide anion, which then reacts with iron (III) to form hydrogen peroxide. Hydrogen peroxide is reduced to hydroxyl radical.

The use of sodium hyaluronate of relatively moderate molecular weight as a supplemental synovial fluid in the leg joint of race horses has been reported (Balazs et al., J. Equine Vet. Sci., p. 217–228, 1985). However, synovial fluid in the joints of humans contains substantially higher molecular weight sodium hyaluronate than that of horses.

Solutions of sodium hyaluronate also have been tested as supplemental synovial fluid for human osteoarthritic joints by injection into the joints. Treatment of arthritis by injection of sodium hyaluronate has been disclosed by Weiss et al., Semin. Arthritis Rheum., 11, p. 143, (1981); Nakimi et al., J. Clin. Pharmcol. Therapy Toxicology, 20, p. 501, (1982); Grecomoro et al., Pharmatherapeutica, 5, p. 137, (1987) and Briganiti et al., Clinical Trials Journal, 24, p. 333, (1987). However, it has been reported that intra-articular injections of sodium hyaluronate solutions do not perform measurably differently from placebos (Dahlberg et al., in "Arthritis & Rheumatism" 37, p.521, 1994). Brown et al. in Ext. Physiol. 76, p.125, (1991), reported that the half-life of hyaluronic acid injected in a joint is only about 13 hours. Dahlberg, vide supra, has disclosed that a 13 hour half-life is short for therapeutic value. It is believed that the short half-life of injected hyaluronic acid is due in part to degradation by hydroxyl radicals (J. M. McCord, Science, 185, p.529, 1974).

This invention relates to novel ways of increasing the resistance of polysaccharides, in particular hyaluronic acid and sodium hyaluronate, to hydroxyl radicals by grafting them with antioxidants.

SUMMARY OF THE INVENTION

This invention pertains to grafted polysaccharide compositions comprising polysaccharide grafted with antioxidant on at least one hydroxyl group of the polysaccharide.

In a preferred embodiment the polysaccharide comprises polysaccharide containing acidic groups. In the most preferred embodiment, the polysaccharide comprises hyaluronic acid or a salt of hyaluronic acid; the antioxidant comprises hindered phenol; and the grafted composition has substantially greater resistance to hydroxyl radicals than does un-grafted hyaluronic acid or its sodium salt.

In another embodiment the invention pertains to a method for grafting a polysaccharide which comprises reacting the polysaccharide with a hydroxyl-reactive derivative of an antioxidant.

In another embodiment the invention also pertains to pharmaceutical compositions for treating inflammation of mammalian joints, e.g., arthritis, for preventing post-operative adhesion formation and for promoting the healing of chronic wounds, comprising as the active component the antioxidant grafted polysaccharide of this invention.

In a further embodiment the invention pertains to drug delivery systems comprising antioxidant grafted polysaccharide which has been crosslinked.

The invention also pertains to cosmetic compositions comprising the grafted polysaccharide of this invention.

In yet another embodiment the invention pertains to methods for treating inflammation of mammalian joints, e.g. arthritis, reducing the incidence of post-operative adhesion formation and promoting the healing of chronic wounds and ulcers comprising injecting or applying an effective amount of a pharmaceutical composition comprising as the active component antioxidant grafted polysaccharide of this invention.

DETAILED DESCRIPTION OF THE INVENTION

The grafted polysaccharide compositions of this invention comprise polysaccharide grafted with antioxidant on at least one hydroxyl group of the polysaccharide.

The compositions of this invention comprise material having a formula selected from the group consisting of:

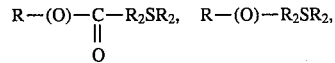

-continued

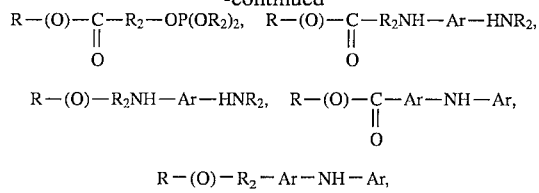

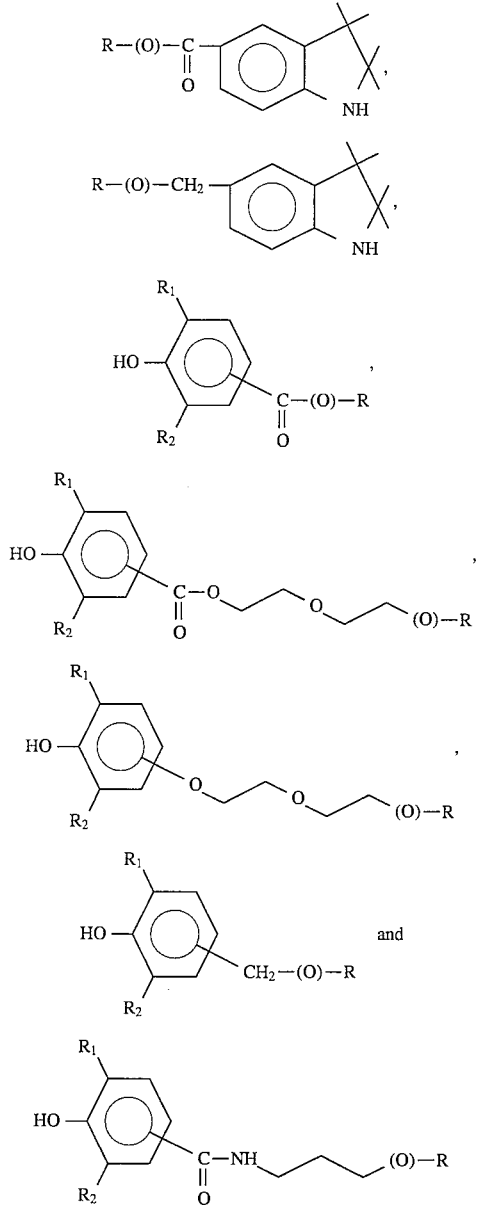

wherein R represents the backbone of polysaccharide or crosslinked polysaccharide containing acidic groups or salts thereof, —(O)— is the residue of a polysaccharide hydroxyl group, $R_1$ is hydrogen, $C_1$–$C_{20}$ alkyl, phenyl or substituted phenyl, $R_2$ is $C_1$–$C_{20}$ alkyl, phenyl or substituted phenyl, and Ar is aryl or substituted aryl.

Preferably the compositions of this invention comprise material having a formula selected from the group consisting of:

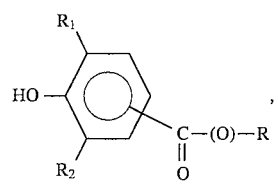

I

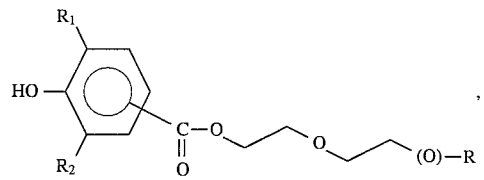

II

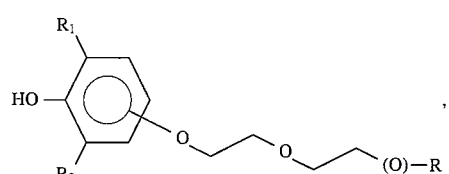

III

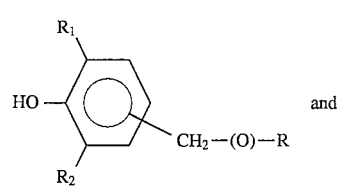

IV and

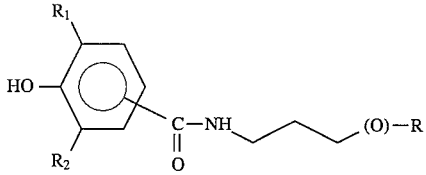

V wherein R represents the backbone of polysaccharide or crosslinked polysaccharide containing acidic groups or salts thereof, —(O)— is the residue of a polysaccharide hydroxyl group; $R_1$ is hydrogen, $C_1$–$C_{20}$ alkyl, phenyl or substituted phenyl; and $R_2$ is $C_1$–$C_{20}$ alkyl, phenyl or substituted phenyl.

In formulas I–V, preferably $R_1$ is selected from the group consisting of hydrogen, methyl, ethyl, i-propyl and t-butyl, and $R_2$ is selected from the group consisting of methyl, ethyl, i-propyl and t-butyl.

More preferably the compositions comprise material of formulas I, II and IV wherein $R_1$ and $R_2$ are t-butyl, and wherein the polysaccharide comprises hyaluronic acid.

The polysaccharides for use in this invention may include, for example, members selected from the group consisting of gum arabic, gum karaya, gum tragacanth, locust bean gum, guar gum, psyllium gum, starch, pectin, agar, alginic acid, furcellaran, dextran, xanthan, carboxymethyl cellulose, methyl cellulose, hydroxyethylcarboxymethyl cellulose, carboxymethyl starch, cationic starch, hyaluronic acid, chondroitin sulfate, keratan sulfate, dermatan sulfate, heparan sulfate, heparin, polygalacturonic acid, polymannuronic acid, polyglucuronic acid and carrageenan.

Preferably the polysaccharides of this invention comprise polysaccharide containing acidic groups or salts of the acidic groups. The preferred acidic groups comprise at least one member selected from the group consisting of carboxyl, sulfate, sulfite and phosphate. The most preferred acidic group is the carboxyl group.

Polysaccharides containing acidic group may include, for example, members selected from the group consisting of hyaluronic acid, chondroitin sulfate, keratan sulfate, dermatan sulfate, heparan sulfate, heparin, carboxymethyl cellulose, hydroxyethylcarboxymethyl cellulose, carboxymethyl starch, pectin, xanthan, alginic acid, polygalacturonic acid, polymannuronic acid, polyglucuronic acid and carrageenan. The most preferred is hyaluronic acid.

The preferred salts in accordance with this invention comprise salts of an alkali or alkaline earth metal, aluminum or ammonium. The most preferred salt is a salt of sodium.

The grafted polysaccharides of this invention may also be crosslinked. Crosslinked polysaccharides may be prepared by any methods disclosed in the art. Sakurai et al. in U.S. Pat. No. 4,716,224, disclose crosslinked hyaluronic acid or salts thereof prepared by crosslinking hyaluronic acid or its salts with a polyfunctional epoxide. In U.S. Pat. No. 4,863,907 Sakurai et al. disclose crosslinked glycosaminoglycan or salts thereof, prepared by crosslinking a glycosaminoglycan or a salt thereof with a polyfunctional epoxy compound. Huang et al., in European Patent Application NO. 0 507 604 A2, disclose ionically crosslinked carboxyl-containing polysaccharides where the crosslinking agent is a compound possessing a trivalent cation. Mälson et al., in U.S. Pat. No. 4,716,154 disclose crosslinking hyaluronic acid with hi- or polyfunctional epoxides or their corresponding halohydrins, epihalohydrins or halides, and divinyl sulfone. Mälson et el., in U.S. Pat. No. 4,772,419 also disclose crosslinking hyaluronic acid with polyfunctional epoxides. In U.S. Pat. No. 4,957,744 della Valle et al. disclose crosslinked esters of hyaluronic acid prepared by esterifying the carboxyl groups of hyaluronic acid with polyhydric alcohols. Balazs et al., in U.S. Pat. Nos. 4,582,865, 4,605,691 and 4,636,524, disclose crosslinking of hyaluronic acid and its salts, and of other polysaccharides, by reaction with divinylsulfone. In U.S. Pat. Nos. 5,128,326 and 4,582,865, Balazs et al. disclose crosslinking hyaluronic acid with formaldehyde, epoxides, polyaziridyl compounds and divinyl sulfone. In U.S. Pat. No. 4,713,448 Balazs et al. disclose chemically modifying hyaluronic acid by reaction with aldehydes such as formaldehyde, glutaraldehyde and glyoxal, and teach the possibility that crosslinking has occurred. In U.S. Pat. No. 5,356,883 Kuo et al. disclose crosslinking hyaluronic acid by reaction with biscarbodiimides. All of the above patents are incorporated herein in their entirety by reference.

A preferred method for crosslinking polysaccharides, by their reaction with di- or polycarboxylic acid anhydrides, is disclosed in co-pending patent application, Ser. No. 362,689, filed Dec. 22, 1994. A preferred crosslinked composition comprises material of above formula I where $R_1$ and $R_2$ are t-butyl, and the polysaccharide is hyaluronic acid or its sodium salt crosslinked by reaction with pyromellitic dianhydride.

In the grafted compositions, the grafting level is most readily expressed in terms of the number of equivalents of antioxidant that are present per equivalent of polysaccharide repeating unit. For the purpose of the invention the minimum level of grafting could be as low as about 1 equivalent of antioxidant per 1000 equivalents of polysaccharide repeating units. A preferred minimum level is about 1 equivalent per 700, and the most preferred minimum level about 1 equivalent per 600 polysaccharide repeating units.

The maximum level of grafting could be as high as about 1 equivalent per 10 equivalents of polysaccharide repeating units. A preferred maximum level is about 1 equivalent per 100, and the most preferred maximum level about 1 equivalent per 400 polysaccharide repeating units.

It has been found that when the antioxidant grafted composition in accordance with this invention is derived from hyaluronic acid or its salts, it has substantially greater resistance to degradation caused by hydroxyl radical than does un-grafted hyaluronic acid or its salts.

In tests for degradation by hydroxyl radical, the hydroxyl radicals were generated by reaction of ferric chloride with ascorbic acid as described by Wong et al. Inorganic Biochemistry, 14, p. 127 (1981), which publication is incorporated herein in its entirety by reference. In a typical test the viscosity half-life was 0.9 hours for hyaluronic acid. When the same test was carried out under the same conditions on grafted compositions, both crosslinked and non-crosslinked, of this invention having formula I wherein R, the polysaccharide, was hyaluronic acid, and $R_1$ and $R_2$ were t-butyl, the viscosity half lives ranged from 3 to 48 hours, indicating the substantially greater resistance of the grafted compositions to degradation by hydroxyl radical.

The antioxidant grafted compositions are prepared by reaction of polysaccharides with hydroxyl-reactive antioxidant derivatives. The term "hydroxyl-reactive antioxidant derivative" is intended to mean an antioxidant containing a functional group capable of reacting with hydroxyl groups contained in a polysaccharide.

The preferred hydroxyl-reactive antioxidants for preparing the compositions of this invention are selected from the group consisting of:

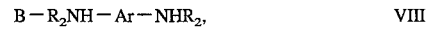

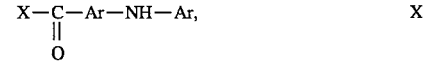

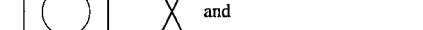

wherein $R_1$ is hydrogen, $C_1$–$C_{20}$ alkyl, phenyl or substituted phenyl; $R_2$ is $C_1$–$C_{20}$ alkyl, phenyl or substituted phenyl; A is —C(O)X, —C(O)OCH$_2$CH$_2$OCH$_2$CH$_2$Y, —C(O)NHCH$_2$CH$_2$CH$_2$Y, —OCH$_2$CH$_2$OCH$_2$CH$_2$Y or —CH$_2$Y; B is —C(O)X, —CH$_2$Y, or X; X is halogen, 1-imidazole, phenoxy, nitrophenoxy, p-toluenesulfonate, methanesulfonate or alkyl or aryl carboxylate; Y is halogen, p-toluenesulfonate and methanesulfonate.

The preferred hydroxyl-reactive antioxidants comprise hydroxyl-reactive hindered phenols of structure XII where $R_1$ is hydrogen, methyl, ethyl, i-propyl or t-butyl, and $R_2$ is methyl, ethyl, i-propyl or t-butyl. The term "hindered phenol" refers to phenols having at least one position ortho to the hydroxyl group occupied by phenyl, substituted phenyl or $C_1$–$C_{20}$ alkyl substituent.

Preferred hydroxyl-reactive hindered phenols of structure XII comprise those wherein $R_1$ and $R_2$ are t-butyl, A is —C(O)X, —CH$_2$Y or —C(O)OCH$_2$CH$_2$OCH$_2$CH$_2$Y, where X is chlorine or 1-imidazole and Y is bromine. Specifically, preferred hydroxyl-reactive hindered phenols are 3,5-di-t-butyl-4-hydroxybenzoyl chloride, 2,6-di-t-butyl-4-bromomethylphenol, 3,5-di-t-butyl-4-hydroxybenzoyl 2-[2-(chloroethoxy)ethoxy]ethyl ester and 3,5-di-t-butyl-4-hydroxybenzoyl-1-imidazole.

Because hydroxyl-reactive antioxidant derivatives may readily react with water, it is preferred that their reaction with polysaccharide be carried out in a dry, polar, aprotic solvent. Preferred solvents are N-methyl pyrrolidinone, N-ethyl pyrrolidinone, N-cyclohexyl pyrrolidinone, 4-methyl morpholine N-oxide, dimethyl formamide, sulfolane and dimethyl sulfoxide.

Salts of acidic polysaccharides may not be soluble in the preferred solvents. In particular, the sodium salt of hyaluronic acid is not soluble in the preferred solvents, and so it is generally convenient for the purpose of this embodiment to convert the sodium salt to a tetraalkyl ammonium salt to increase solubility. After the grafting reaction of tetraalkyl ammonium salt and hydroxyl-reactive antioxidant derivative, the product can be converted back to the sodium form by ion exchange.

If it is desired to prepare an antioxidant grafted crosslinked composition, the crosslinking reaction can be carried out either before or after the grafting reaction. It may also be carried out simultaneously with the grafting reaction in those cases where the solvents used for crosslinking are the same as those used for the grafting reaction.

In the grafting reaction, the ratio of hydroxyl-reactive antioxidant derivative to polysaccharide is most readily expressed in terms of the moles of antioxidant derivative utilized per equivalent of repeating unit in the polysaccharide. For the purpose of the invention, the minimum level of hydroxyl-reactive antioxidant derivative could be as low as about 1 equivalent per 1000 equivalents of polysaccharide repeating units. A preferred minimum level is about 1 equivalent per 700, and the most preferred minimum level about 1 equivalent per 600 polysaccharide repeating units.

The maximum level of hydroxyl-reactive antioxidant derivative could be as high as about 1 equivalent per 10 equivalents of polysaccharide repeating units. A preferred maximum level is about 1 equivalent per 100, and the most preferred maximum level about 1 equivalent per 400 polysaccharide repeating units.

As noted above, in other embodiments the invention pertains to compositions for treating inflamed mammalian joints, e.g., arthritis, for preventing post-operative adhesions and for promoting the healing of chronic wounds and ulcers. The active component of these compositions comprises the antioxidant grafted polysaccharides of this invention. The preferred antioxidant grafted polysaccharides are hindered-phenol grafted hyaluronic acid or hindered-phenol grafted crosslinked hyaluronic acid, or pharmaceutically acceptable salts thereof.

Pharmaceutically acceptable salts include salts of an alkali or alkaline earth metal, aluminum or ammonium. The preferred pharmaceutically acceptable salt is sodium.

The antioxidant grafted polysaccharide compositions of this invention can be used to prevent post-operative adhesions in any animal that is susceptible to unwanted adhesion formation following surgery. The compositions are used to prevent adhesions from developing in mammals, preferably human beings. They are useful in all types of surgery where it is desired to inhibit the formation of post-surgical adhesions, e.g., abdominal surgery, gynecological surgery, thoracic surgery, orthopedic surgery, neurological surgery and ophthalmological surgery. The preferred compositions for this use are hindered-phenol grafted hyaluronic acid or hindered-phenol grafted crosslinked hyaluronic acid, or pharmaceutically acceptable salts thereof.

Adhesion preventatives may be administered to the site of surgical trauma by any convenient mode such as, for example, by lavage, by coating directly on the site in a gel, cream, film or foam, or by any other convenient method. The administration of adhesion preventatives can occur at any time before significant wound healing has occurred. It is preferred to administer it at the conclusion of surgery, just prior to closing of the wound. However, in some cases it may be desirable to administer the preventative continually over a period of time. An effective amount of adhesion preventative is an amount necessary to affect a reduction in the incidence of post-operative surgical adhesions. Preferably, the amount should be enough to coat the entire area exposed to the surgical trauma, and if desired an additional amount sufficient to coat body tissue adjacent to the area of trauma.

The antioxidant grafted polysaccharide compositions of this invention can also be used to promote the healing of chronic wounds, e.g. burns, and ulcers, e.g. diabetes foot ulcers in mammals, in particular, human beings. The preferred compositions for this use are hindered-phenol grafted hyaluronic acid or hindered-phenol grafted crosslinked hyaluronic acid, or pharmaceutically acceptable salts thereof. Hyaluronic acid retains moisture and also has angiogenesis characteristics that make it useful for this application. When utilized for wound healing the compositions may be used alone in aqueous solution, preferably physiological saline solution, or the solutions may be combined with wound healing drugs and other water soluble polymers. They may be administered to the site of the wound or ulcer by any convenient mode such as, for example, by lavage, by coating directly on the site in a gel, cream, film or foam, by impregnation in a bandage or wound dressing that is applied to wound or ulcer, or by any other convenient method. An effective amount to promote healing is enough to coat the entire area of the wound or ulcer and if desired an additional amount sufficient to coat body tissue adjacent to the wound or ulcer. A typical antioxidant grafted polysaccharide may contain as other ingredients water-soluble polymers, antibiotics, immunosuppressants and pain reducers.

In the application of grafted hyaluronic acid or crosslinked grafted hyaluronic acid of this invention to the treatment of inflamed joints, e.g., arthritis, in mammals, in particular human beings, the hyaluronic acid derivative is usually dissolved in physiological saline to a sufficient viscosity to pass through an injection needle. The maximum viscosity is about 50,000 cps, preferably about 30,000 cps. The minimum viscosity is about 5,000 cps. The treatment solution is then injected into the diseased joint.

A typical knee joint synovial fluid supplementation injection procedure is similar to one described by Miller et al. in J. Bone and Joint Surgery, 40, p.636 (1985), which publication is incorporated herein by reference. A sterile solution, 2.5 ml, of the sodium salt of antioxidant grafted hyaluronic acid (concentration of grafted hyaluronic acid: 10 mg/ml) in buffered saline (sodium chloride 8.5 mg/ml, dibasic sodium phosphate 0.537 mg/ml, sodium dihydrogen phosphate 0.016 mg/ml) is slowly drawn into a syringe to ensure the absence of air pockets. The knee is then prepared for injection by cleaning with soap, wiping with cetyl trimethylammonium bromide and painting with tincture of iodine. The solution is injected into a synovium cavity through a premarked triangular arc at the lateral side of the joint bound by the tibial plateau, the edge of the ligamentum patellae, and the curve of the lateral femoral condyle. Local anaesthesia may be used prior to injection. In certain cases knee aspiration with the buffered saline solution may be needed prior to the synovial fluid supplementation injection. Such a procedure is described by Dahlberg et al. in Arthritis & Rheumatism, 37, 1994, page 521, which article is incorporated herein by reference.

The injectable solution may contain materials in addition to the grafted composition. These include water soluble polymers such as chondroitin sulfate, dermatan sulfate, and/or a phospholipid to improve the lubricity of the solution. Anesthetics, anti-inflammatory reagents, antibiotics, antibacterials, cytotoxins and sugars may be added also.

Antioxidant grafted polysaccharides of this invention particularly in the crosslinked form, may be used as a drug delivery system. The preferred compositions for this use are hindered-phenol grafted hyaluronic acid or hindered-phenol grafted crosslinked hyaluronic acid, or pharmaceutically acceptable salts thereof. Crosslinked hyaluronic acid forms a molecular cage in which molecules with pharmacological activity can be dispersed. The substances contained in the cage are delivered into the environment by diffusion. The drug molecule, or mixture of drug molecules, may be covalently or non-covalently bonded to the hyaluronic acid. The covalent bonding can be via attachment to the carboxylic acid or hydroxyl groups of the hyaluronic acid moieties. The gels, films, threads, particles or sponges of hyaluronic acid-based composition may be placed, sprayed, ingested, injected or implanted at the location where the contained pharmacological substance is needed. These substances may be therapeutic drugs (such as anesthetics, analgesics, anti-inflammatories, diuretics, antagonists, antibiotics, hormones, antirheumatics, adrenergic agonists, cytostatics, antihypertensives or immunosuppressant agents}, growth factors, enzymes or cellular anti-adhesion compounds.

Antioxidant grafted polysaccharides of this invention can also function as components of cosmetics for topical uses. The preferred compositions for this use are hindered-phenol grafted hyaluronic acid or hindered-phenol grafted crosslinked hyaluronic acid, or pharmaceutically acceptable salts thereof. Because hyaluronic acid has been shown to hold moisture under low relative humidity conditions and yield a pleasant and smooth feeling at high relative humidities, it has been used as a moisturizer in cosmetic formulations. The compositions of this invention will provide similar effects. Mixtures of the grafted hyaluronic acid compositions with other low cost water-soluble polymers such as carboxymethyl cellulose, pectin, alginate, soy protein, casein and gelatin may also be employed.

Natural extracts of plant sources, such as cactus aloe vera, mesquite, matricaria chamomilla, tumeric, carrot, jojoba, rose and others, may be blended into a cosmetic formulation containing grafted hyaluronic acid. Alpha hydroxy acids such as lactic and hydroxyethanoic may be added to the formulation to improve the plasticity of the skin.

A typical anti-aging cosmetic composition is: 2-hydroxyethanoic acid, 7%, propylene glycol, 15%, hindered-phenol grafted hyaluronic acid solution (1 g/100 ml), 1%, water, 60% and ethyl alcohol, 17%, where all percentages are by weight.

A formulation for facial soft gel is: aqueous slurry of carboxymethyl cellulose (3 g/100 ml), 25%, aqueous solution of triethanolamine (10 g/100 ml), 11%, Methyl Gluceth-10, 5%, hindered-phenol grafted hyaluronic acid aqueous solution (1 g/100 ml), 1%, perfume and preservatives, 1%, water, 57%, where all percentages are be weight.

A typical essential skin moisturizer composition is hydroxyethyl cellulose, 0.5%, Methyl Gluceth-10, 2%, glycerin, 2%, hindered-phenol grafted hyaluronic acid aqueous solution (1 g/100 ml), 1%, water, 94%, preservatives and perfume, 0.5%, where all percentages are by weight.

The invention is illustrated by the following examples, which are provided for the purpose of representation, and are not to be construed as limiting the scope of the invention. All parts and percentages in the examples are by weight unless otherwise specified.

EXAMPLE 1

Synthesis of 3,5-di-t-butyl-4-hydroxybenzoyl chloride

A mixture of 3,5-di-t-butyl-4-hydroxybenzoic acid (4 grams), 20 ml of hexane and 20 ml of thionyl chloride was boiled for 4.5 hours. The solvent and excess thionyl chloride were removed by distillation, leaving a solid which was used without further purification. To confirm the identity of the acid chloride, a small sample was quenched with excess anhydrous ethanol and triethylamine. The quenched sample as extracted with water and methylene chloride. After the solvent was evaporated, an oil was obtained. The $^1$H NMR spectrum ($CDCl_3$, ppm from TMS) confirmed that the oil was the corresponding ester: 7.9 ppm (s, Ar, 2), 5.25 ppm (S, OH, 1), 4.3 ppm (q, $CH_3$, 18) and 1.44 ppm (t, $CH_3$, 3). This result confirms that 3,5-di-t-butyl-4-hydroxybenzoyl chloride has been formed.

EXAMPLE 2

Synthesis of 2,6-di-t-butyl-4-bromomethyl phenol

A mixture of 1 g of 2,6-di-t-butyl-4-methyl phenol, 0.9 g of N-bromosuccinimide and 40 ml of carbon tetrachloride was boiled for 1.5 hours. Succinimide was removed by filtration, and the resulting organic solution was evaporated to give a viscous liquid with the following $^1$H NMR spectrum ($CDCl_3$, ppm from TMS): 7.05 ppm (s, ArH, 2), 5,15 ppm (s, OH, 1), 4.35 ppm (s, $CH_2Br$, 2) and 1.3 ppm (s, $CH_3$, 18).

EXAMPLE 3

Synthesis of 3,5-di-t-butyl-4-hydroxybenzoyl-2-[2-(2-chloroethoxy)ethoxy]ethyl ester In a 250 ml flask equipped with a Dean-Stark trap, a mixture of 5 g of 3,5-di-t-butyl-4-hydroxybenzoic acid, 3.7 g of 2-[2-(2-chloroethoxy)ethoxy]ethanol, 0.1 g of p-toluenesulfonic acid and 60 ml of toluene was heated at boiling for 4 days. The resulting mixture was extracted with water and methylene chloride, and then the methylene chloride solution was dried over $MgSO_4$. Evaporation of the solvent gave 6.97 g of the ester with the following $^1$H NMR spectrum ($CDCl_3$, ppm from TMS): 7.9 ppm (s, ArH, 2), 5.72 ppm (s, OH, 1), 5.45 ppm (m, $CH_2$, 2), 3.86 ppm (m, $CH_2$, 2), 3.7 ppm (m, $CH_2$, 6), 3.6 ppm (m, $CH_2$, 2) and 2.45 ppm (s, $CH_3$, 18).

EXAMPLE 4

Synthesis of 3,5-di-t-butyl-4-hydroxybenzoyl-1-imidazole

A mixture of 1 g of 3,5-di-t-butyl-4-hydroxybenzoic acid, 0.7 g of 1,1'-dicarbonyl diimidazole and 50 ml of methylene chloride was stirred together at room temperature for 17 hours. After the solvent was removed, the product was recrystallized in toluene and hexane to yield a hygroscopic solid. A small sample of the solid was mixed with 0.2 g of ethanol and 2 ml of methylene chloride and allowed to stand for 10 hours. After the solvent was removed, only the corresponding ethyl ester was identified by $^1$H NMR as in Example 1. This result indicated that 3,5-di-t-butyl-4-hydroxybenzoyl-1-imidazole had been formed.

EXAMPLE 5

Preparation of the methyltricaprylammonium salt of hyaluronic acid

To a solution of 10 g of sodium hyaluronate (fermentation product, Chisso Corporation, Chiba, Japan) in 1000 ml of water was added a solution of 50 g. of methyltricaprylammonium chloride (Aliquat 336, Aldrich Chemical, Milwaukee, Wis.) in 50 ml of acetone. The mixture was stirred overnight, and then the rubbery precipitate was filtered, washed with water and acetone, and then dried in vacuo overnight. It was again soaked in 500 ml of acetone for 7 hours and dried in vacuo overnight to yield 46.9 g of rubbery material.

EXAMPLE 6

Grafting 3,5-di-t-butyl-4-hydroxybenzoyl chloride to hyaluronic acid

To a solution of 10 g of the methyltricaprylammonium salt of hyaluronic acid (prepared by the method of Example 5) in 1000 ml of dry N-methylpyrrolidinone (NMP), 0.4 g of 3,5-di-t-butyl-4-hydroxybenzoyl chloride (Example 1) was added. The mixture was tumbled for 3 hours and then stored at 10° C. for 16 hours. For ion exchange back to the sodium salt, an aqueous solution of NaCl (15 g in 250 ml of water) was then added to the reaction mixture. After the resulting solution had been stirred for 1 hour, 3 g of sodium bicarbonate and 200 ml of acetone were added to precipitate the product. The polymer was filtered and washed five times with acetone/water (ratio: 4/1, 200 ml) and then with 100 ml of acetone. The product was further purified by redissolving it in 1 l of water and then precipitating it into a large volume of methanol. Four grams of product was obtained.

EXAMPLE 7

Grafting 3,5-di-t-butyl-4-hydroxybenzoyl-1-imidazole to hyaluronic acid

To a solution of 2 g of the methyltricaprylammonium salt of hyaluronic acid (prepared by the method of Example 5) in 280 ml of NMP was added 0.25 g of 3,5-di-t-butyl-4-hydroxybenzoyl-1-imidazole (Example 4). The mixture was maintained at 45° C. for 20 hours, and then it was ion exchanged back to the sodium salt form as described in Example 6. The product weighed 0.92 g.

EXAMPLE 8

Grafting 3,5-di-t-butyl-4-hydroxybenzoyl chloride to hyaluronic acid crosslinked with the diglycidyl ether of bisphenol A The crosslinking reaction was carried out first, by mixing 2 g of the methyltricaprylammonium salt of hyaluronic acid (prepared by the method of Example 5), 0.2 g of diglycidyl ether of bisphenol A, and 280 ml of NMP, and maintaining the mixture at 45° C. for 24 hours. To this mixture was then added 0.2 g of 3,5-di-t-butyl-4hydroxybenzoyl chloride, and then the entire reaction mixture was maintained at room temperature for 17 hours. The product was converted to the sodium salt and worked up as described for Example 6.

EXAMPLE 9

Grafting 3,5-di-t-butyl-4-hydroxybenzoyl chloride to hyaluronic acid crosslinked with 1,2,4,5-benzenetetracarboxylic acid dianhydride To a solution of 5 g of the methyltricaprylammonium salt of hyaluronic acid (prepared by the method of Example 5) in 700 ml of NMP, there was added 0.5 g of 1,2,4,5-benzenetetracarboxylic acid dianhydride. The mixture was maintained at 10° C. for 7 days. Triethyl amine (1 ml) and 3,5-di-t-butyl-4-hydroxybenzoyl chloride (0.5 g) were then added to the reaction mixture. After 16 hours, the product was ion exchanged with a solution of NaCl (0.5 g) and NaHCO$_3$ (0.5 g) in 50 ml of water, and then precipitated by addition of 400 ml of acetone. The product was filtered and washed with 4/1 acetone/water and then pure acetone. After drying 2.9 g of polymer was obtained.

EXAMPLE 10

Grafting of 3,5-di-t-butyl-4-hvdroxybenzoyl-2-[2-(2-chloroethoxy)ethoxy ethyl ester to hyaluronic acid A mixture of 2 g of methyltricaprylammonium salt of hyaluronic acid (prepared by the method of Example 5) and 0.25 g of 3,5-di-t-butyl-4-hydroxybenzoyl-2-[2-(2-chloroethoxy)ethoxy]ethyl ester in 280 ml of NMP was maintained at 45° C. for 20 hours. The mixture was treated with a solution of 0.1 g NaCl and 0.1 g of NaHCO$_3$ in 20 ml of water and worked up as in Example 9. After drying 1.0 g of polymer was obtained.

EXAMPLE 11

Resistance of grafted hyaluronic acid to degradation by hydroxyl radicals

Hydroxyl radicals were generated by the reaction of ferric ion with ascorbic acid as described by Wong et al. Inorganic Biochemistry, 14, p. 127 (1981).

To a 100 ml aqueous solution of sodium salt of hindered-phenol grafted hyaluronate 0.3 to 0.6% wt/vol as indicated, buffered at pH 7.4) 0.25 ml of a ferric chloride solution (1.1 g in 20 ml of water) and 0.25 ml of an ascorbic acid solution (0.64 g in 20 ml of water) were added. The mixture was shaken for about 10 seconds, and then the first viscosity (Brookfield) was measured after 10 minutes. The viscosity at this point was considered to be 100%. The degradation resistance of the sample was assessed by measuring the time required to reduce the viscosity to 50% of the 10 minute value (viscosity half-life). The control consisted of sodium hyaluronate. The results are in table 1.

TABLE 1

Ferric Chloride/Ascorbic Acid Test of Hindered-Phenol Grafted Hyaluronic Acid

| Product of Example | Sample Concentration, % Wt./Vol. | Viscosity Half-Life, hrs |
| --- | --- | --- |
| Control | 0.4 | 0.9 |
| 6 | 0.4 | 3 |
| 7 | 0.3 | 4.5 |
| 8 | 0.34 | 5 |
| 9 | 0.6 | 48 |
| 10 | 0.3 | 5 |

While the invention has been described with respect to specific embodiments, it should be understood that they are not intended to be limiting and that many variations and modifications are possible without departing from the scope of this invention.

What is claimed is:

1. A grafted polysaccharide composition comprising polysaccharide grafted with antioxidant on at least one hydroxyl group of the polysaccharide.

2. The composition of claim 1 wherein the antioxidant comprises a hindered phenol.

3. The composition of claim 1 wherein the grafted polysaccharide composition is crosslinked.

4. The composition of claim 1 wherein the polysaccharide is one or more members selected from the group consisting of gum arabic, gum karaya, gum tragacanth, locust bean gum, guar gum, psyllium gum, starch, pectin, agar, alginic acid, furcellaran, dextran, xanthan, carboxymethyl cellulose, methyl cellulose, hydroxyethylcarboxymethyl cellulose, carboxymethyl starch, cationic starch, hyaluronic acid, chondroitin sulfate, keratan sulfate, dermatan sulfate, heparan sulfate, heparin, polygalacturonic acid, polymannuronic acid, polyglucuronic acid and carrageenan.

5. The composition of claim 1 wherein the polysaccharide contains acidic groups or salts thereof.

6. The composition of claim 5 wherein the acidic groups are selected from the group consisting of carboxyl, sulfate, sulfite and phosphate.

7. The composition of claim 5 wherein the acidic groups comprise carboxyl.

8. The composition of claim 5 wherein the polysaccharide is selected from the group consisting of hyaluronic acid, chondroitin sulfate, keratan sulfate, dermatan sulfate, heparan sulfate, heparin, carboxymethyl cellulose, hydroxyethylcarboxymethyl cellulose, carboxymethyl starch, pectin, xanthan, alginic acid, polygalacturonic acid, polymannuronic acid, polyglucuronic acid and carrageenan.

9. The composition of claim 5 wherein the salts comprise salts of an alkali or alkaline earth metal, aluminum or ammonium.

10. The composition of claim 5 wherein the grafted polysaccharide comprises grafted hyaluronic acid.

11. The composition of claim 10 wherein the hyaluronic acid is crosslinked.

12. The composition of claim 5 wherein the grafted polysaccharide comprises a salt of grafted hyaluronic acid.

13. The composition of claim 12 wherein the salt of grafted hyaluronic acid comprises a salt of alkali or alkaline earth metal, aluminum or ammonium.

14. The composition of claim 12 wherein the salt of grafted hyaluronic acid comprises a sodium salt.

15. The composition of claim 3 wherein the crosslinked polysaccharide comprises polysaccharide that has been crosslinked by reaction with di- or polycarboxylic acid anhydride.

16. The composition of claim 15 wherein the polysaccharide is hyaluronic acid.

17. The composition of claim 1 wherein grafted antioxidant is present at a minimum level of about 1 equivalent per 1000 repeating units of polysaccharide.

18. The composition of claim 1 wherein grafted antioxidant is present at a minimum level of about 1 equivalent per 700 repeating units of polysaccharide.

19. The composition of claim 1 wherein grafted antioxidant is present at a minimum level of about 1 equivalent per 600 repeating units of polysaccharide.

20. The composition of claim 1 wherein grafted antioxidant is present at a maximum level of about 1 equivalent per 10 repeating units of polysaccharide.

21. The composition of claim 1 wherein grafted antioxidant is present at a maximum level of about 1 equivalent per 100 repeating units of polysaccharide.

22. The composition of claim 1 wherein grafted antioxidant is present at a maximum level of about 1 equivalent per 400 repeating units of polysaccharide.

23. The composition of claim 1 wherein grafted antioxidant is present at a level of from about 1 equivalent per 400 to about 1 equivalent per 600 repeating units of polysaccharide.

24. The composition of claim 1 wherein the grafted polysaccharide is selected from the group consisting of:

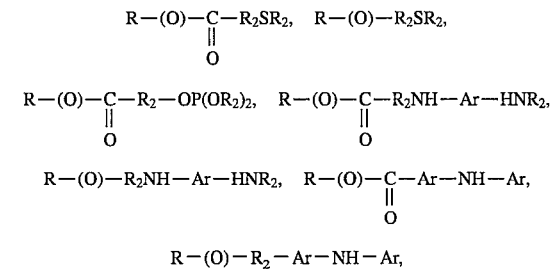

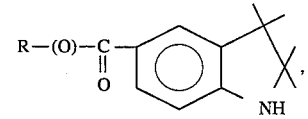

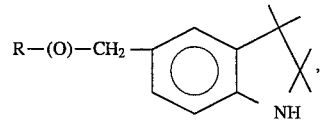

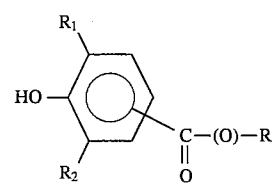

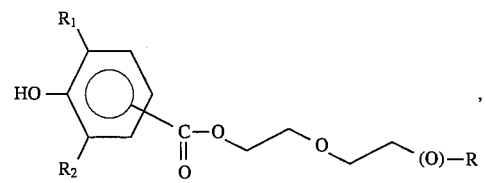

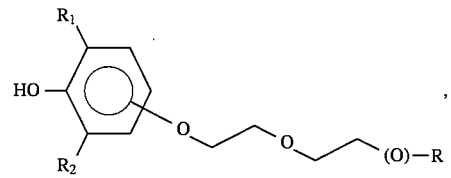

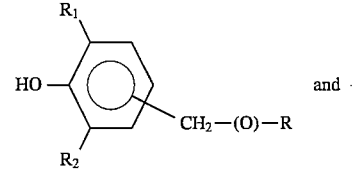

and

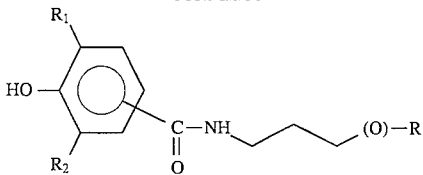

wherein R represents the backbone of polysaccharide or crosslinked polysaccharide containing acidic groups or salts thereof, —(O)— is the residue of a polysaccharide hydroxyl group, $R_1$ is hydrogen, $C_1$–$C_{20}$ alkyl, phenyl or substituted phenyl, $R_2$ is $C_1$–$C_{20}$ alkyl, phenyl or substituted phenyl, and Ar is aryl or substituted aryl.

25. The composition of claim 1 wherein the grafted polysaccharide is selected from the group consisting of:

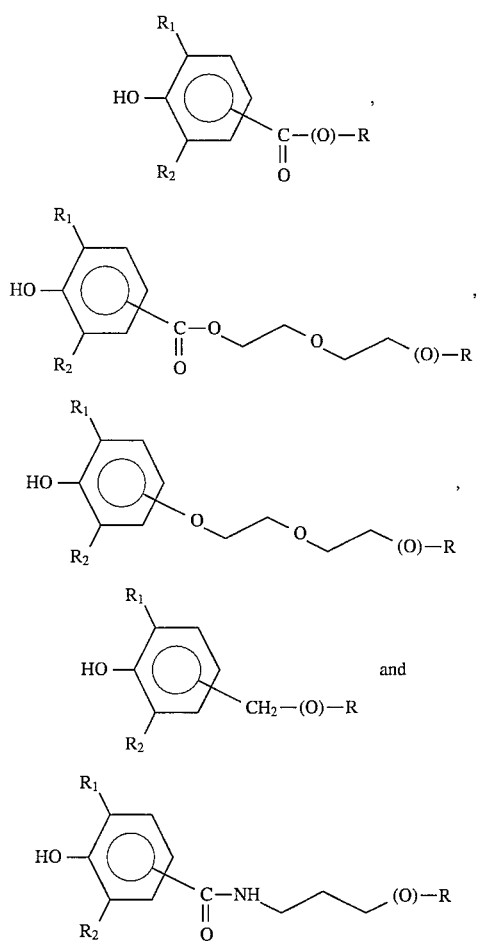

wherein R represents the backbone of polysaccharide containing acidic groups or salts thereof, —(O)— is the residue of a polysaccharide hydroxyl group, $R_1$ is hydrogen, $C_1$–$C_{20}$ alkyl, phenyl or substituted phenyl, and $R_1$ is $C_1$–$C_{20}$ alkyl, phenyl or substituted phenyl.

26. The composition of claim 25 wherein $R_1$ is selected from the group consisting of hydrogen, methyl, ethyl, i-propyl and t-butyl, and $R_2$ is selected from the group consisting of methyl, ethyl, i-propyl and t-butyl.

27. The composition of claim 24 wherein the grafted polysaccharide is crosslinked.

28. The composition of claim 27 wherein the polysaccharide comprises polysaccharide that has been crosslinked by reaction with di- or polycarboxylic acid anhydride.

29. The composition of claim 24 wherein the polysaccharide is selected from the group consisting of hyaluronic acid, chondroitin sulfate, keratan sulfate, dermatan sulfate, heparan sulfate, heparin, carboxymethyl cellulose, hydroxyethylcarboxymethyl cellulose, carboxymethyl starch, pectin, xanthan, alginic acid, polygalacturonic acid, polymannuronic acid, polyglucuronic acid and carrageenan.

30. The composition of claim 25 wherein the grafted polysaccharide comprises material of formula I wherein $R_1$ and $R_2$ are t-butyl.

31. The composition of claim 25 wherein the grafted polysaccharide comprises material of formula IV wherein $R_1$ and $R_2$ are t-butyl.

32. The composition of claim 25 wherein the grafted polysaccharide comprises material of formula II wherein $R_1$ and $R_2$ are t-butyl.

33. The composition of claim 25 wherein the polysaccharide comprises hyaluronic acid.

34. The composition of claim 30 wherein the polysaccharide comprises hyaluronic acid.

35. The composition of claim 34 wherein the hyaluronic acid is crosslinked by reaction with pyromellitic dianhydride.

36. The composition of claim 31 wherein the polysaccharide comprises hyaluronic acid.

37. The composition of claim 32 wherein the polysaccharide comprises hyaluronic acid.

38. The composition of claim 10 wherein the grafted hyaluronic acid has greater resistance to hydroxyl radicals than does un-grafted hyaluronic acid, the viscosity half-life of an aqueous solution of the grafted hyaluronic acid being greater than that of an aqueous solution of hyaluronic acid when treated with hydroxyl radicals under the same conditions.

39. The composition of claim 14 wherein the sodium salt of grafted hyaluronic acid has greater resistance to hydroxyl radicals than does the sodium salt of hyaluronic acid, the viscosity half-life of an aqueous solution of the grated sodium salt of hyaluronic acid being greater than that of an aqueous solution of sodium salt of hyaluronic acid when treated with hydroxyl radicals under the same conditions.

40. A method for preparing polysaccharide grafted with antioxidant on at least one hydroxyl group of the polysaccharide, comprising reacting said polysaccharide with at least one hydroxyl-reactive antioxidant derivative selected from the group consisting of:

| | |
|---|---|
| 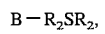 B—$R_2$S$R_2$, | VI |
| 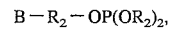 B—$R_2$—OP(O$R_2$)$_2$, | VII |
| 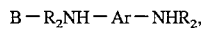 B—$R_2$NH—Ar—NH$R_2$, | VIII |
| 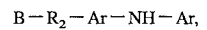 B—$R_2$—Ar—NH—Ar, | IX |
| 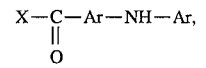 X—C(=O)—Ar—NH—Ar, | X |
| 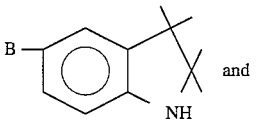 and | XI |

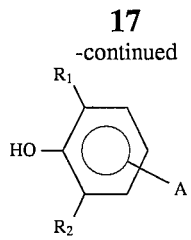

wherein R₁ is hydrogen, $C_1$–$C_{20}$ alkyl, phenyl or substituted phenyl; R₂ is $C_1$–$C_{20}$ alkyl, phenyl or substituted phenyl; A is —C(O)X, —C(O)OCH₂CH₂OCH₂CH₂Y, —C(O)NHCH₂CH₂CH₂Y, —OCH₂CH₂OCH₂CH₂Y or —CH₂Y; B is —C(O)X, —CH₂Y, or X; X is halogen, 1-imidazole, phenoxy, nitrophenoxy, p-toluenesulfonate, methanesulfonate, alkyl carboxylate or aryl carboxylate; Y is halogen, p-toluenesulfonate or methanesulfonate.

41. The method of claim 40 wherein the polysaccharide is one or more members selected from the group consisting of gum arabic, gum karaya, gum tragacanth, locust bean gum, guar gum, psyllium gum, starch, pectin, agar, alginic acid, furcellaran, dextran, xanthan, carboxymethyl cellulose, methyl cellulose, hydroxyethylcarboxymethyl cellulose, carboxymethyl starch, cationic starch, hyaluronic acid, chondroitin sulfate, keratan sulfate, dermatan sulfate, heparan sulfate, heparin, polygalacturonic acid, polymannuronic acid, polyglucuronic acid and carrageenan.

42. The method of claim 40 wherein the polysaccharide contains acidic groups or salts thereof.

43. The method of claim 42 wherein the acidic groups are selected from the group consisting of carboxyl, sulfate, sulfite and phosphate.

44. The method of claim 42 wherein the polysaccharide containing acidic groups or salts thereof, is selected from the group consisting of hyaluronic acid, chondroitin sulfate, keratan sulfate, dermatan sulfate, heparan sulfate, heparin, carboxymethyl cellulose, hydroxyethylcarboxymethyl cellulose, carboxymethyl starch, pectin, xanthan, alginic acid, polygalacturonic acid, polymannuronic acid, polyglucuronic acid and carrageenan.

45. The method of claim 40 wherein the grafted polysaccharide composition is crosslinked.

46. The method of claim 40 wherein the polysaccharide comprises hyaluronic acid.

47. The method of claim 40 wherein the polysaccharide comprises a salt of hyaluronic acid.

48. The method of claim 47 wherein the salt comprises a salt of an alkali or alkaline earth metal, aluminum or ammonium.

49. The method of claim 48 wherein the salt comprises a sodium salt.

50. The method of claim 47 wherein the salt of hyaluronic acid is converted to tetraalkylammonium salt before reaction with hydroxyl-reactive antioxidant.

51. The method of claim 50 wherein the tetraalkylammonium salt is converted to a sodium salt after reaction with hydroxyl-reactive antioxidant.

52. The method of claim 50 wherein the reaction is carried out in polar, non-protic solvent selected from the group consisting of N-methyl pyrrolidinone, N-ethyl pyrrolidinone, N-cyclohexyl pyrrolidinone, 4-methyl morpholine N-oxide, dimethyl formamide, sulfolane and dimethyl sulfoxide.

53. The method of claim 40 wherein hydroxyl-reactive antioxidant derivative is used at a minimum level of about 1 equivalent per 1000 repeating units of polysaccharide.

54. The method of claim 40 wherein hydroxyl-reactive antioxidant derivative is used at a minimum level of about 1 equivalent per 700 repeating units of polysaccharide.

55. The method of claim 40 wherein hydroxyl-reactive antioxidant derivative is used at a minimum level of about 1 equivalent per 600 repeating units of polysaccharide.

56. The method of claim 40 wherein hydroxyl-reactive antioxidant derivative is used at a maximum level of about 1 equivalent per 10 repeating units of polysaccharide.

57. The method of claim 40 wherein hydroxyl-reactive antioxidant derivative is used at a maximum level of about 1 equivalent per 100 repeating units of polysaccharide.

58. The method of claim 40 wherein hydroxyl-reactive antioxidant derivative is used at a maximum level of about 1 equivalent per 400 repeating units of polysaccharide.

59. The method of claim 52 wherein the polysaccharide is hyaluronic acid, the solvent is N-methyl pyrrolidinone, and the hydroxyl-reactive antioxidant is 3,5-di-t-butyl-4-hydroxybenzoyl chloride at a level of from about 1 equivalent per 10 to about 1 equivalent per 1000 repeating units of the hyaluronic acid.

60. The composition of claim 13 wherein the salt of grafted hyaluronic acid comprises a pharmaceutically acceptable salt.

61. A composition for applying to a wound for healing, comprising a wound healing effective amount of the grafted polysaccharide of claim 1 in a pharmaceutically acceptable carrier.

62. The composition of claim 61 wherein the grafted polysaccharide comprises grafted hyaluronic acid.

63. The composition of claim 62 wherein the hyaluronic acid is present as a pharmaceutically acceptable salt.

64. The composition of claim 63 wherein the pharmaceutically acceptable salt comprises a salt of an alkali or alkaline earth metal, aluminum or ammonium.

65. A cosmetic composition comprising an effective amount of the grafted polysaccharide of claim 1 in a cosmetic vehicle.

66. The cosmetic composition of claim 65 wherein the grafted polysaccharide comprises grafted hyaluronic acid.

67. The cosmetic composition of claim 66 wherein the grafted hyaluronic acid is present as a pharmaceutically acceptable salt.

68. The cosmetic composition of claim 67 wherein the pharmaceutically acceptable salt comprises a salt of an alkali or alkaline earth metal, aluminum or ammonium.

69. The composition of claim 1 wherein the polysaccharide is one or more members selected from the group consisting of gum arabic, gum karaya, gum tragacanth, locust bean gum, guar gum, psyllium gum, furcellaran and xanthan.

70. The composition of claim 1 wherein the polysaccharide is one or more members selected from the group consisting of starch, carboxymethyl starch and cationic starch.

71. The composition of claim 1 wherein the polysaccharide is pectin.

72. The composition of claim 1 wherein the polysaccharide is one or more members selected from the group consisting of agar, alginic acid, polygalacturonic acid, polymannuronic acid, polyglucuronic acid and carrageenan.

73. The composition of claim 1 wherein the polysaccharide is dextran.

74. The composition of claim 1 wherein the polysaccharide is one or more members selected from the group consisting of carboxymethyl cellulose, methyl cellulose and hydroxyethylcarboxymethyl cellulose.

75. The composition of claim 1 wherein the polysaccharide is one or more members selected from the group consisting of chondroitin sulfate, keratan sulfate and dermatan sulfate.

76. The composition of claim 1 wherein the polysaccharide is one or more members selected from the group consisting of heparan sulfate and heparin.

77. The method of claim 40 wherein the polysaccharide is one or more members selected from the group consisting of gum arabic, gum karaya, gum tragacanth, locust bean gum, guar gum, psyllium gum, furcellaran and xanthan.

78. The method of claim 40 wherein the polysaccharide is one or more members selected from the group consisting of starch, carboxymethyl starch and cationic starch.

79. The method of claim 40 wherein the polysaccharide is pectin.

80. The method of claim 40 wherein the polysaccharide is one or more members selected from the group consisting of agar, alginic acid, polygalacturonic acid, polymannuronic acid, polyglucuronic acid and carrageenan.

81. The method of claim 40 wherein the polysaccharide is dextran.

82. The method of claim 40 wherein the polysaccharide is one or more members selected from the group consisting of carboxymethyl cellulose, methyl cellulose and hydroxyethylcarboxymethyl cellulose.

83. The method of claim 40 wherein the polysaccharide is one or more members selected from the group consisting of chondroitin sulfate, keratan sulfate and dermatan sulfate.

84. The method of claim 40 wherein the polysaccharide is one or more members selected from the group consisting of heparan sulfate and heparin.

* * * * *